United States Patent
Takumi et al.

(10) Patent No.: US 9,469,596 B2
(45) Date of Patent: Oct. 18, 2016

(54) METHOD FOR REMOVING QUATERNARY SALT

(71) Applicant: ARAKAWA CHEMICAL INDUSTRIES, LTD., Osaka-shi (JP)

(72) Inventors: Kiyoshi Takumi, Osaka (JP); Naoki Sasagawa, Tsukuba (JP); Yoichiro Ezaki, Tsukuba (JP)

(73) Assignee: ARAKAWA CHEMICAL INDUSTRIES, LTD., Osaka-shi (JP)

( * ) Notice: Subject to any disclaimer, the term of this patent is extended or adjusted under 35 U.S.C. 154(b) by 0 days.

(21) Appl. No.: 14/370,344

(22) PCT Filed: Jan. 28, 2013

(86) PCT No.: PCT/JP2013/051735
§ 371 (c)(1),
(2) Date: Jul. 2, 2014

(87) PCT Pub. No.: WO2013/121869
PCT Pub. Date: Aug. 22, 2013

(65) Prior Publication Data
US 2015/0031918 A1    Jan. 29, 2015

(30) Foreign Application Priority Data

Feb. 14, 2012 (JP) ................................ 2012-029371

(51) Int. Cl.
*C07C 209/86* (2006.01)
*B01D 11/04* (2006.01)

(52) U.S. Cl.
CPC ......... *C07C 209/86* (2013.01); *B01D 11/0492* (2013.01)

(58) Field of Classification Search
None
See application file for complete search history.

(56) References Cited

U.S. PATENT DOCUMENTS

| | | |
|---|---|---|
| 4,072,713 A | 2/1978 | Bjornson |
| 6,310,232 B1 | 10/2001 | Ofori |
| 6,469,191 B1 | 10/2002 | Reisinger et al. |
| 2008/0045636 A1 | 2/2008 | Iyama et al. |

FOREIGN PATENT DOCUMENTS

| | | |
|---|---|---|
| CN | 1331670 A | 1/2002 |
| CN | 1481336 A | 3/2004 |
| CN | 101089112 A | 12/2007 |
| EP | 0 763 521 A2 | 3/1997 |
| JP | S49-55608 | 5/1974 |
| JP | H09-136034 | 5/1997 |
| JP | 2007-181833 A1 | 7/2007 |
| JP | 2008-246287 A1 | 10/2008 |
| JP | 2010-70480 A1 | 4/2010 |
| WO | 0248049 A1 | 6/2002 |

OTHER PUBLICATIONS

The English translation of Yamaguchi et al. JP 2008246287.*
Office Action dated Nov. 11, 2015 for the corresponding CN patent application No. 201380009405.5, with translation.
Office Action dated Mar. 12, 2015 in CN patent application No. 201380009405.5.
Handbook of Phase Transfer Catalysis; Blackie Academic & Professional; London; 1997; pp. 127-128, cover sheet and table of contents (5 Sheets total).
International Search Report for International Application No. PCT/JP2013/051735 dated Apr. 23, 2013.
Office Action issued on Apr. 28, 2016 in the corresponding Chinese patent application No. 201380009405.5 with translation.

* cited by examiner

*Primary Examiner* — Clinton Brooks
*Assistant Examiner* — Jennifer C Sawyer
(74) *Attorney, Agent, or Firm* — Kratz, Quintos & Hanson, LLP

(57) ABSTRACT

The purpose of the present invention is to provide a method for efficiently removing a quaternary salt from an organic solvent. The present invention relates to a method for removing a quaternary salt, the method including: contacting a solution of a quaternary salt in an organic solvent with an aqueous solution containing at least one member selected from the group consisting of (a1) compounds having one or more anionic functional groups and (a2) polymers having at least one member selected from the group consisting of carboxyl group and sulfonic acid group, thereby removing the quaternary salt from the organic solvent.

5 Claims, No Drawings

METHOD FOR REMOVING QUATERNARY SALT

TECHNICAL FIELD

The present invention relates to a method for removing a quaternary salt.

BACKGROUND ART

Quaternary salts, such as alkyl ammonium salts and the like, are used in a wide range of fields; for example, quaternary salts are used as surfactants, phase-transfer catalysts, ion-conductive electrolytes, starting materials for photoresist developer solutions, antiseptics, antistats, and dispersants. Because these compounds are expensive, it is preferable to recover them for recycle. However, because the recycling of such quaternary salts requires, for example, the step of recovering the organic solution by concentration, and the step of extracting the quaternary salt from wastewater, time and effort are problematically required. Thus, for efficiently recycling or efficiently carrying out after-treatment, the efficient removal of a quaternary salt from a solution beforehand is of economic importance in industrial manufacturing processes. Thus far, the following have been suggested as quaternary salt removal methods.

For example, Non-patent Document 1 and Patent Document 1 disclose the extraction of a quaternary salt from an organic solvent by the use of water.

Patent Document 2 discloses the removal of a quaternary salt by washing a quaternary salt-containing organic solution with water, and subjecting the washings to extraction with methylene chloride.

Further, Patent Document 3 reports the removal of a quaternary salt by adsorption with the use of an activated carbon, Patent Document 4 reports the adsorption of a surfactant with the use of cyclodextrin, and Patent Document 5 reports the removal of a quaternary salt by adsorption with the use of an ion-exchange resin.

CITATION LIST

Patent Document

Patent Document 1: U.S. Pat. No. 6,310,232
Patent Document 2: JPH09-136034A
Patent Document 3: JP2010-070480A
Patent Document 4: JP2008-246287A
Patent Document 5: JP2007-181833A

Non-Patent Document

Non-patent Document 1: Handbook of Phase Transfer Catalysis, Blackie Academic, London (1997), p. 127

SUMMARY OF INVENTION

Technical Problem

However, the extraction methods using water as disclosed in Non-patent Document 1 and Patent Document 1 are disadvantageous in that although highly hydrophilic quaternary salts can be extracted by such methods, highly hydrophobic quaternary salts form an emulsion, and separation by such methods is thus impossible or takes time. When extracting such highly hydrophilic quaternary salts, the removal efficiency can be somewhat increased by frequent extraction; however, this results in a problematic increase of wastewater. The method disclosed in Patent Document 2 is not environmentally preferable due to its use of a halogenated solvent, and the method can only be used in limited circumstances. The adsorption method disclosed in Patent Document 3 requires a large amount of adsorbent to completely remove a quaternary salt because substances other than the desired quaternary salt are also adsorbed, thereby lowering the adsorption capacity. The adsorption method disclosed in Patent Document 4 is not applicable to organic solvent systems because quaternary salts form an emulsion in organic solution systems. The adsorption method disclosed in Patent Document 5 is disadvantageous in that the removal efficiency is poor because the ammonium ion concentration must be kept low, thus increasing wastewater. The method disclosed in Patent Document 5 is not expected to produce effects such as the removal of a quaternary salt from an organic solvent because of the poor wettability of ion functional groups of the ion-exchange resin used in an organic solvent system. Therefore, none of the above methods are satisfactory from a technical standpoint, and none are necessarily advantageous for industrial application from an environmental and economic perspective.

An object of the present invention is to provide a method for efficiently removing a quaternary salt from an organic solvent.

Solution to Problem

To achieve the above object, the present inventors conducted extensive research on methods for removing a quaternary salt from a solution of the quaternary salt in an organic solvent, and found that the use of an aqueous solution comprising one or more specific compounds makes it possible to remove a quaternary salt from an organic solvent. Accordingly, the inventors completed the present invention.

Specifically, the present invention provides the following methods for removing a quaternary salt.

Item 1. A method for removing a quaternary salt, the method comprising contacting a solution of a quaternary salt in an organic solvent with an aqueous solution containing at least one member selected from the group consisting of (a1) compounds having one or more anionic functional groups and (a2) polymers having at least one member selected from the group consisting of carboxyl group and sulfonic acid group, thereby removing the quaternary salt from the organic solvent.

Item 2. The method for removing a quaternary salt according to Item 1, wherein the solution of a quaternary salt in an organic solvent has previously been washed with an alkaline aqueous solution.

Item 3. The method for removing a quaternary salt according to Item 1 or 2, wherein the quaternary salt is an ammonium salt.

Item 4. The method for removing a quaternary salt according to any one of Items 1 to 3, wherein the quaternary salt has a total of 10 to 40 carbon atoms.

Item 5. The method for removing a quaternary salt according to any one of Items 1 to 4, wherein component (a1) is at least one member selected from the group consisting of acetic acid, carbonic acid, succinic acid, maleic acid, glutaric acid, malonic acid, citric acid, tartaric acid, gluconic acid, phosphoric acid, pyrophosphoric acid, polyphosphoric acid, and alkali metal salts thereof.

Item 6. The method for removing a quaternary salt according to any one of Items 1 to 5, wherein component (a2) is at least one member selected from the group consisting of polyacrylic acid, polymaleic acid, polystyrene sulfonic acid, carboxymethyl cellulose, alkali metal salts thereof, and alkali metal partial salts thereof.

Item 7. The method for removing a quaternary salt according to any one of Items 1 to 6, wherein the aqueous solution is adjusted to a pH of 1.5 to 13.5.

Advantageous Effects of Invention

The present invention enables the efficient removal of a quaternary salt from a solution of the quaternary salt in an organic solvent. Because, compared to the prior art methods, a quaternary salt is removed using a relatively inexpensive removal agent with simple operations, the method according to the present invention significantly reduces the burden on the industrial manufacturing process, thus being economically advantageous. The method can be employed in a wide range of fields, such as medical drugs, analysis, chemical synthesis, and semiconductors.

DESCRIPTION OF EMBODIMENTS

The present invention is directed to a method for removing a quaternary salt from an organic solvent by contacting a solution of the quaternary salt in the organic solvent with an aqueous solution containing at least one member selected from the group consisting of (a1) compounds having one or more anionic functional groups, and (a2) polymers having at least one member selected from the group consisting of carboxyl group and sulfonic acid group.

The compounds (a1) (hereinafter referred to as "component (a1)"), which have one or more anionic functional groups, for use in the method for removing a quaternary salt according to the present invention are not particularly limited as long as the compounds are those having one or more anionic functional groups in a molecule, or the salts thereof; and known compounds can be used. Examples of anionic functional groups include carboxyl group, sulfonic acid group, and phosphoric acid group. Examples of the salts include alkali metal salts and alkaline earth metal salts. Preferable salts are alkali metal salts, and particularly more preferable salts are sodium salts because they are commercially readily available.

Examples of compounds that can be used as component (a1) include: compounds having one or more carboxyl groups, such as acetic acid, (meth)acrylic acid, carbonic acid, succinic acid (anhydride), maleic acid (anhydride), fumaric acid, glutaric acid, adipic acid, malonic acid, citric acid, tartaric acid, gluconic acid, oxalic acid, adipic acid, terephthalic acid, phthalic acid (anhydride), aspartic acid, and glutamic acid; compounds having one or more sulfonic acid groups, such as p-toluenesulfonic acid, benzenesulfonic acid, and methanesulfonic acid; compounds having one or more phosphoric acid groups, such as phosphoric acid, pyrophosphoric acid, and polyphosphoric acid; and salts of these compounds. These compounds and salts can be used singly, or in a combination of two or more. Among them, acetic acid, carbonic acid, succinic acid, maleic acid, glutaric acid, malonic acid, citric acid, tartaric acid, gluconic acid, phosphoric acid, pyrophosphoric acid, polyphosphoric acid, and alkali metal salts thereof are particularly preferable. The amount of component (a1) for use is selected from the range of 0.5 to 20 times, and preferably 1 to 10 times, that of the quaternary salt contained in the solution to be treated on a weight basis. An amount below this range results in lowered quaternary salt removal efficiency, thus requiring multiple treatments. An amount above this range results in enhanced quaternary salt removal efficiency; however, it is not advantageous from an economic standpoint because component (a1) is added in an amount that is more than necessary. The concentration or the pH of the aqueous solution is suitably adjusted in accordance with the type of the solution to be treated. It is preferable to adjust the amount of component (a1) and water so that the aqueous solution has a concentration in the range of 1 to 30 wt %. It is preferable to adjust the pH with sulfuric acid, sodium hydroxide, or the like, so that the pH falls within the range of 1.5 to 13.5.

The polymers (a2) (hereinafter, referred to as "component (a2)"), which have at least one member selected from the group consisting of carboxyl group and sulfonic acid group, for use in the method for removing a quaternary salt according to the present invention are not particularly limited, as long as the polymers are those obtained by polymerizing one or more monomers having at least one member selected from the group consisting of carboxyl group and sulfonic acid group, or the salts thereof; and known polymers can be used. Examples of the salts include alkali metal salts and alkaline earth metal salts, with alkali metal salts being preferable, and sodium salts being particularly preferable.

Examples of component (a2) include: polymers having carboxyl groups, such as poly(meth)acrylic acid, polymaleic acid, carboxymethyl cellulose, polyaspartic acid, polyglutamic acid, alginic acid, and (meth)acrylic acid/maleic acid copolymers; polymers having sulfonic acid groups, such as polystyrene sulfonic acid; polymers having carboxyl groups and sulfonic acid groups, such as (meth)acrylic acid/sulfonic acid copolymers; and alkali metal salts thereof. The degree of neutralization of alkali metal salts is preferably in the range of, but not particularly limited to, 10 to 90%. Among the above substances, polyacrylic acid, polymaleic acid, polystyrene sulfonic acid, carboxymethyl cellulose, alkali metal salts thereof, and alkali metal partial salts thereof are preferable. In this specification, the alkali metal salts thereof refer to polymers completely converted to their alkali metal salts, and the alkali metal partial salts thereof refer to polymers partially converted to their alkali metal salts. Particularly preferable as component (a2) are polyacrylic acid and polymaleic acid. The amount of component (a2) for use is 0.5 to 5.0 times, preferably 1 to 2.5 times, that of the quaternary salt contained in the solution to be treated on a weight basis. An amount below this range results in lowered quaternary salt removal efficiency, thus requiring multiple treatments. An amount above this range results in enhanced quaternary salt removal efficiency; however, it is not advantageous from an economic standpoint because component (a2) is added in an amount that is more than necessary. The molecular weight of the polymer for use is not particularly limited; however, the weight average molecular weight (polystyrene equivalent value as measured by gel permeation chromatography) can be selected from the range of 500 to 200,000, preferably 1,000 to 100,000, from the viewpoint of liquid separation or operability. The concentration or the pH of the aqueous solution of the polymer is suitably adjusted in accordance with the type of the solution to be treated. It is preferable to adjust the amount of component (a2) and water so that the aqueous solution has a concentration in the range of 1 to 20 wt %. It is preferable to adjust the pH with sulfuric acid, sodium hydroxide, or the like, so that that the pH falls within the range of 1.5 to 13.5.

Component (a1) and component (a2) may be used in combination. When using components (a1) and (a2) in combination, the amount of each component for use is not particularly limited; however, component (a2) is typically used in an amount of 10 to 500 parts by weight per 100 parts by weight of component (a1). The concentration of the mixture of components (a1) and (a2) in an aqueous solution is preferably adjusted to, but not particularly limited to, 1 to 20 wt %. The pH is preferably adjusted to fall within the range of 1.5 to 13.5.

The present invention is directed to a method for removing a quaternary salt by contacting a solution of the quaternary salt in an organic solvent with an aqueous solution containing component (a1) and/or component (a2). The temperature at which the solution of the quaternary salt in an organic solvent is contacted with the aqueous solution is typically, but not limited to, 0 to 100° C., with 20 to 60° C. being preferable. A temperature of 20° C. or more particularly enhances liquid separation and improves workability; however, a temperature exceeding 60° C. requires time and energy for heating up, further requiring time and energy for cooling when separating liquids. The time period during which the solution of the quaternary salt in an organic solvent is in contact with the aqueous solution is typically, but not particularly limited to, 1 to 180 minutes, with 5 to 60 minutes being preferable. 5 minutes or more of contact increases the quaternary salt removal efficiency; however, contact for a time period exceeding 60 minutes substantially achieves equilibrium, at which point it thereafter becomes difficult to further increase the removal efficiency.

It is preferable to wash a solution of a quaternary salt in an organic solvent with an alkaline aqueous solution before contacting the solution with an aqueous solution containing component (a1) and/or component (a2). Washing with an alkaline aqueous solution enhances liquid separation, operability, and quaternary salt removal efficiency. Examples of alkaline aqueous solutions for use include sodium hydroxide, potassium hydroxide, lithium hydroxide, calcium hydroxide, ammonium hydroxide, and tetramethylammonium hydroxide.

Examples of quaternary salts to be removed by the method for removing a quaternary salt according to the present invention include quaternary ammonium salts and quaternary phosphonium salts. Specific examples of quaternary ammonium salts to which the present invention is applicable include trioctylmethylammonium salts, trioctylethylammonium salts, tridecylmethylammonium salts, trialkylmethylammonium salts (mixtures of trioctyl/tridecylmethylammonium salts), trihexadecylmethylammonium salts, dialkyldimethylammonium salts (mixtures of di(C8-C18 alkyl)dimethylammonium salts), dilauryldimethylammonium salts, didecyldimethylammonium salts, dioctyldimethylammonium salts, dioleoyldimethylammonium salts, lauryltrimethylammonium salts, stearyltrimethylammonium salts, lauryldimethylbenzylammonium salts, distearyldimethylammonium salt, tricaprylmethylammonium salts, tetrabutylammonium salts, benzyltrimethylammonium salts, benzyltriethylammonium salts, benzyltributylammonium salts, tetrapentylammonium salts, tetrabutylammonium salts, and tetramethylammonium salts. Specific examples of quaternary phosphonium salts include tetraphenylphosphonium salts, tetra-n-ethylphosphonium salts, tetra-n-propylphosphonium salts, tetra-n-butylphosphonium salts, di-n-decyldimethylphosphonium salts, di-n-octadecyldimethylphosphonium salts, tri-n-decylmethylphosphonium salts, benzyltributylphosphonium salts, phenyltrimethylphosphonium salts, and tetraphenylphosphonium salts. Preferable quaternary salts include ammonium salts. Although the anion moieties of these salts are not particularly limited, specific examples thereof include chloride ion, bromide ion, iodide ion, hydroxide ion, nitrate ion, sulfate ion, hydrogen sulfate ion, acetate ion, carbonate ion, hydrogen carbonate ion, phosphate ion, and hydrogen phosphate ion. The method according to the present invention produces an excellent effect in removing, among the above quaternary salts, a quaternary salt having a total of 10 to 40 carbon atoms, and particularly in removing trioctylmethylammonium salts, trialkylmethylammonium salts (mixtures of trioctyl/tridecylmethylammonium salts), dialkyldimethylammonium salts (mixtures of di(C8-C18 alkyl)dimethylammonium salts), dilauryldimethylammonium salts, didecyldimethylammonium salts, and dioctyldimethylammonium salts.

The solvent used for an organic solvent solution to which the method for removing a quaternary salt according to the present invention is applied is not particularly limited, as long as it is not miscible with water. Specific examples of the solvent include toluene, xylene, chloroform, chlorobenzene, o-dichlorobenzene, dichlorotoluene, dichloromethane, dichloroethane, hexane, cyclohexane, ethyl acetate, butyl acetate, and diethyl ether. In particular, the quaternary salt removal efficiency is enhanced when toluene is used.

According to the above-described method of the present invention, the use of an aqueous solution containing component (a1) and/or component (a2) enables efficient removal of a quaternary salt from a solution of the quaternary salt in an organic solvent. Because the method of the present invention enables the removal of a quaternary salt by the use of an inexpensive removal agent with simple operations as compared with the conventional methods, the method significantly reduces the burden on the industrial manufacturing process, thus being economically advantageous. Further, the use of the method according to the present invention enables the recovery or recycling of a quaternary salt. The method can be employed in a wide range of fields, such as medical drugs, analysis, chemical synthesis, and semiconductors.

EXAMPLES

The following examples illustrate the methods according to the present invention.

Example 1

50 g of a solution of 0.8 g of trioctylmethylammonium chloride, as a quaternary salt, in toluene was contacted with 30 g of a solution of 6.3 g of polyphosphoric acid, as a removal agent, in water by agitation of the two phases at 25° C. for 30 minutes. Subsequently, the organic phase was separated from the aqueous phase, and concentrated under reduced pressure at 60° C. for 1 hour using an evaporator, followed by measurement of the weight of the obtained quaternary salt. The removal rate of the quaternary salt was calculated from the weight of the quaternary salt contained in the organic phase before and after the treatment according to the following equation, and the removal rate was 74%.

Removal Rate (%)=(weight of quaternary salt contained in organic phase before treatment−weight of quaternary salt contained in organic phase after treatment)×100/weight of quaternary salt contained in organic phase before treatment

Example 2

The same procedure as described in Example 1 was repeated except that the removal agent was replaced by 2.6 g of glutaric acid. The removal rate of the quaternary salt was 75%.

Example 3

The same procedure as described in Example 1 was repeated except that the quaternary salt was replaced by 0.75 g of dialkyldimethylammonium chloride (a mixture of di(C8-C18 alkyl)dimethylammonium chlorides). The removal rate of the quaternary salt was 70%.

Example 4

The same procedure as described in Example 3 was repeated except that the removal agent was replaced by 4.6 g of pyrophosphoric acid. The removal rate of the quaternary salt was 89.0%.

Example 5

The same procedure as described in Example 1 was repeated except that the quaternary salt and the removal agent were replaced by 0.80 g of didecyldimethylammonium chloride and 1.8 g of sodium acetate, respectively. The removal rate of the quaternary salt was 98.8%.

Example 6

The same procedure as described in Example 5 was repeated except that the removal agent was replaced by 1.8 g of sodium hydrogen carbonate. The removal rate of the quaternary salt was 80.0%.

Example 7

The same procedure as described in Example 5 was repeated except that the removal agent was replaced by 2.2 g of phosphoric acid. The removal rate of the quaternary salt was 86.3%.

Example 8

The same procedure as described in Example 5 was repeated except that the removal agent was replaced by 3.6 g of pyrophosphoric acid. The removal rate of the quaternary salt was 93.8%.

Example 9

The same procedure as described in Example 5 was repeated except that the removal agent was replaced by 7.0 g of polyphosphoric acid. The removal rate of the quaternary salt was 90.0%.

Example 10

The same procedure as described in Example 5 was repeated except that the removal agent was replaced by 2.2 g of succinic acid, and the aqueous solution was adjusted to a pH of 13.5 with sodium hydroxide. The removal rate of the quaternary salt was 91.3%.

Example 11

The same procedure as described in Example 5 was repeated except that the removal agent was replaced by 2.9 g of glutaric acid, and the aqueous solution was adjusted to a pH of 13.5 with sodium hydroxide. The removal rate of the quaternary salt was 97.5%.

Example 12

The same procedure as described in Example 5 was repeated except that the removal agent was replaced by 4.2 g of citric acid, and the aqueous solution was adjusted to a pH of 13.5 with sodium hydroxide. The removal rate of the quaternary salt was 91.3%.

Example 13

The same procedure as described in Example 1 was repeated except that removal agent was replaced by 1.6 g of sodium polyacrylate (molecular weight: 2,000, polystyrene equivalent value as measured by gel permeation chromatography; hereinafter, the molecular weight of the removal agent refers to a polystyrene equivalent value as measured by gel permeation chromatography), and the aqueous solution was adjusted to a pH of 2.0 with sulfuric acid. The removal rate of the quaternary salt was 93.8%.

Example 14

The same procedure as described in Example 1 was repeated except that the removal agent was replaced by 1.6 g of sodium polyacrylate (molecular weight: 6,000), and the aqueous solution was adjusted to a pH of 1.7 with sulfuric acid. The removal rate of the quaternary salt was 92.5%.

Example 15

The same procedure as described in Example 1 was repeated except that the removal agent was replaced by 1.6 g of sodium polyacrylate (molecular weight: 50,000), and the aqueous solution was adjusted to a pH of 1.6 with sulfuric acid. The removal rate of the quaternary salt was 98.8%.

Example 16

The same procedure as described in Example 1 was repeated except that the removal agent was replaced by 1.6 g of polyacrylic acid (molecular weight: 6,000) (pH 2.0). The removal rate of the quaternary salt was 86.3%.

Example 17

The same procedure as described in Example 1 was repeated except that the removal agent was replaced by polymaleic acid manufactured by NOF corporation (trade name: Nonpol (registered trademark) PMA-50W), which was used in an amount of 1.6 g based on the solids content (pH 1.4). The removal rate of the quaternary salt was 86.3%.

Example 18

The same procedure as described in Example 1 was repeated except that the removal agent was replaced by 1.6 g of sodium salt of acrylic acid/sulfonic acid copolymer (molecular weight: 6,000), and the aqueous solution was adjusted to a pH of 2.0 with sulfuric acid. The removal rate of the quaternary salt was 96.3%.

Example 19

The same procedure as described in Example 3 was repeated except that the removal agent was replaced by 1.6 g of sodium polyacrylate (molecular weight: 2,000) (pH: 8.0). The removal rate of the quaternary salt was 75.0%.

Example 20

The same procedure as described in Example 3 was repeated except that the removal agent was replaced by 1.6 g of sodium polyacrylate (molecular weight: 50,000) (pH: 8.3). The removal rate of the quaternary salt was 97.0%.

Example 21

The same procedure as described in Example 3 was repeated except that the removal agent was replaced by 1.6 g of polyacrylic acid (molecular weight: 6,000) (pH: 2.0). The removal rate of the quaternary salt was 88.0%.

Example 22

The same procedure as described in Example 3 was repeated except that the removal agent was replaced by 1.6 g of sodium polystyrene sulfonate (molecular weight: 70,000), and the aqueous solution was adjusted to a pH of 1.1 with sulfuric acid. The removal rate of the quaternary salt was 92.0%.

Example 23

The same procedure as described in Example 3 was repeated except that the removal agent was replaced by 1.6 g of sodium salt of poly(acrylic acid/maleic acid) (molecular weight: 60,000) (pH: 7.9). The removal rate of the quaternary salt was 81.3%.

Example 24

The same procedure as described in Example 3 was repeated except that the removal agent was replaced by 1.6 g of sodium salt of acrylic acid/sulfonic acid copolymer (molecular weight: 6,000) (pH: 7.3). The removal rate of the quaternary salt was 68.0%.

Example 25

The same procedure as described in Example 5 was repeated except that the removal agent was replaced by 1.6 g of polyacrylic acid (molecular weight: 6,000) (pH: 2.0). The removal rate of the quaternary salt was 99.0%.

Example 26

The same procedure as described in Example 5 was repeated except that the removal agent was replaced by 1.6 g of sodium polyacrylate (molecular weight: 6,000), and the aqueous solution was adjusted to a pH of 13.5 with sodium hydroxide. The removal rate of the quaternary salt was 96.3%.

Example 27

The same procedure as described in Example 5 was repeated except that the removal agent was replaced by 1.6 g of sodium polystyrene sulfonate (molecular weight: 70,000) (pH: 5.4). The removal rate of the quaternary salt was 91.3%.

Example 28

The same procedure as described in Example 16 was repeated except that 50 g of a solution of 0.8 g of trioctyl-methylammonium chloride, as a quaternary salt, in toluene was treated in advance with 32 g of a solution of 0.8 g of sodium hydroxide in water. The removal rate of the quaternary salt was 95.0%.

Example 29

The same procedure as described in Example 17 was repeated except that 50 g of a solution of 0.8 g of trioctyl-methylammonium chloride, as a quaternary salt, in toluene was treated in advance with 32 g of a solution of 0.8 g of sodium hydroxide in water. The removal rate of the quaternary salt was 92.2%.

Comparative Example 1

The same procedure as described in Example 1 was repeated except that the removal agent was not used. The removal rate of the quaternary salt was 9.3%.

Comparative Example 2

The same procedure as described in Example 1 was repeated except that the removal agent was not used, and the aqueous solution was adjusted to a pH of 1.2 with sulfuric acid. The removal rate of the quaternary salt was 0%.

Comparative Example 3

The same procedure as described in Example 1 was repeated except that the removal agent was not used, and the aqueous solution was adjusted to a pH of 13.5 with sodium hydroxide. The removal rate of the quaternary salt was 1.3%.

Comparative Example 4

The same procedure as described in Example 3 was repeated except that the removal agent was not used. Due to emulsion formation, separation was impossible.

Comparative Example 5

The same procedure as described in Example 3 was repeated except that the removal agent was not used, and the aqueous solution was adjusted to a pH of 1.2 with sulfuric acid. The removal rate of the quaternary salt was 0%.

Comparative Example 6

The same procedure as described in Example 3 was repeated except that the removal agent was not used, and the aqueous solution was adjusted to a pH of 13.5 with sodium hydroxide. The removal rate of the quaternary salt was 17.3%.

Comparative Example 7

The same procedure as described in Example 5 was repeated except that the removal agent was not used. Due to emulsion formation, separation was impossible.

Comparative Example 8

The same procedure as described in Example 5 was repeated except that the removal agent was not used, and the aqueous solution was adjusted to a pH of 1.2 with sulfuric acid. The removal rate of the quaternary salt was 0%.

Comparative Example 9

The same procedure as described in Example 5 was repeated except that the removal agent was not used, and the aqueous solution was adjusted to a pH of 13.5 with sodium hydroxide. The removal rate of the quaternary salt was 21.3%.

The invention claimed is:

1. A method for removing a quaternary salt, the method comprising
contacting the solution of a quaternary salt in an organic solvent with an aqueous solution containing (a2) a polymer having at least one member selected from the group consisting of carboxyl group and sulfonic acid group, thereby removing the quaternary salt from the organic solvent,
wherein the solvent is at least one member selected from the group consisting of toluene, xylene, chloroform, chlorobenzene, o-dichlorobenzene, dichlorotoluene, dichloromethane, dichloroethane, hexane, cyclohexane, ethyl acetate, butyl acetate, and diethyl ether, and wherein component (a2) is at least one member selected from the group consisting of polyacrylic acid, polymaleic acid, polystyrene sulfonic acid, carboxymethyl cellulose, alkali metal salts thereof, and alkali metal partial salts thereof.

2. The method for removing a quaternary salt according to claim 1, wherein the solution of a quaternary salt in an organic solvent has previously been washed with an alkaline aqueous solution.

3. The method removing a quaternary salt according to claim 1, wherein the quaternary salt is an ammonium salt.

4. The method for removing a quaternary salt according to claim 1, wherein the quaternary salt has a total of 10 to 40 carbon atoms.

5. The method for removing a quaternary salt according to claim 1, wherein the aqueous solution is adjusted to a pH of 1.5 to 13.5.

* * * * *